United States Patent
Johns

(10) Patent No.: US 10,092,523 B2
(45) Date of Patent: *Oct. 9, 2018

(54) LONG ACTING PHARMACEUTICAL COMPOSITIONS

(71) Applicant: GlaxoSmithKline Intellectual Property (No. 2) Limited, Brentford, Middlesex (GB)

(72) Inventor: Brian Alvin Johns, Research Triangle Park, NC (US)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 14 days.

This patent is subject to a terminal disclaimer.

(21) Appl. No.: 15/514,564

(22) PCT Filed: Sep. 24, 2015

(86) PCT No.: PCT/IB2015/057360
§ 371 (c)(1),
(2) Date: Mar. 27, 2017

(87) PCT Pub. No.: WO2016/046786
PCT Pub. Date: Mar. 31, 2016

(65) Prior Publication Data
US 2017/0246118 A1  Aug. 31, 2017

Related U.S. Application Data

(60) Provisional application No. 62/055,779, filed on Sep. 26, 2014.

(51) Int. Cl.
| | | |
|---|---|---|
| *A61K 31/56* | (2006.01) | |
| *A61K 9/50* | (2006.01) | |
| *A61K 9/10* | (2006.01) | |
| *A61K 9/00* | (2006.01) | |
| *A61K 31/505* | (2006.01) | |
| *A61K 31/4985* | (2006.01) | |
| *A61K 47/10* | (2017.01) | |

(52) U.S. Cl.
CPC .......... *A61K 9/5031* (2013.01); *A61K 9/0019* (2013.01); *A61K 9/10* (2013.01); *A61K 31/4985* (2013.01); *A61K 31/505* (2013.01); *A61K 31/56* (2013.01); *A61K 47/10* (2013.01)

(58) Field of Classification Search
CPC ........ A61K 9/0019; A61K 47/10; A61K 9/10; A61K 9/5031; A61K 31/4985; A61K 31/505; A61K 31/56
USPC ...................................................... 514/171
See application file for complete search history.

(56) References Cited

U.S. PATENT DOCUMENTS

| | | |
|---|---|---|
| 5,034,394 A | 7/1991 | Daluge |
| 5,358,721 A | 10/1994 | Guittard et al. |
| 9,102,685 B2 | 8/2015 | Johns |
| 2003/0026843 A1 | 2/2003 | Bogue |
| 2005/0142205 A1 | 6/2005 | Rashba-Step et al. |
| 2006/0205697 A1 | 9/2006 | Robinson et al. |
| 2007/0197646 A1 | 8/2007 | Bradbury et al. |
| 2008/0206161 A1 | 8/2008 | Tamarkin et al. |
| 2009/0023698 A1 | 1/2009 | Krasutsky et al. |
| 2009/0275583 A1 | 11/2009 | Yager et al. |
| 2010/0190795 A1 | 7/2010 | Yli-Kauhaluoma et al. |
| 2011/0144071 A1 | 6/2011 | Grawe et al. |
| 2011/0218204 A1 | 9/2011 | Reddy et al. |
| 2011/0282055 A1 | 11/2011 | Yoshida et al. |
| 2012/0046291 A1 | 2/2012 | Nitz et al. |
| 2012/0302534 A1 | 11/2012 | Gao et al. |
| 2014/0357643 A1 | 12/2014 | Johns |
| 2015/0218142 A1 | 8/2015 | Hatcher et al. |
| 2015/0313917 A1 | 11/2015 | Cai et al. |
| 2016/0120878 A1 | 5/2016 | Hatcher et al. |

FOREIGN PATENT DOCUMENTS

| | | | |
|---|---|---|---|
| CN | | 104844679 A | 8/2015 |
| EP | | 0349242 A2 | 1/1990 |
| WO | | 200190046 A1 | 11/2001 |
| WO | | 2005112929 A2 | 12/2005 |
| WO | WO | 2006/106103 A2 | 10/2006 |
| WO | | 2006117666 A2 | 11/2006 |
| WO | | 2007141389 A1 | 12/2007 |
| WO | | 2007141390 A1 | 12/2007 |
| WO | | 2007141391 A1 | 12/2007 |
| WO | | 2007141392 A2 | 12/2007 |
| WO | WO | 2007/147882 A2 | 12/2007 |
| WO | | 2008057420 A2 | 5/2008 |
| WO | | 2009082818 A1 | 7/2009 |
| WO | | 2009082819 A1 | 7/2009 |
| WO | | 2010053817 A1 | 5/2010 |
| WO | | 2010054606 A2 | 5/2010 |
| WO | | 2011007230 A2 | 1/2011 |

(Continued)

OTHER PUBLICATIONS

Andrews Chasity D et al: "Long-acting integrase inhibitor protects macaques from intrarectal simian/human immunodeficiency virus" Science; vol. 343 No. 6175, Mar. 2014, pp. 1151-1154.

(Continued)

*Primary Examiner* — Barbara P Badio
(74) *Attorney, Agent, or Firm* — Robert H. Brink; Edward R. Gimmi; William R. Majarian

(57) ABSTRACT

The present invention relates to long acting pharmaceutical compositions or pharmaceutically acceptable salts thereof, useful in the treatment or prevention of Human Immunodeficiency Virus (HIV) infections.

57 Claims, 3 Drawing Sheets

(56) References Cited

FOREIGN PATENT DOCUMENTS

| WO | 2011100308 A1 | 8/2011 |
|---|---|---|
| WO | WO 2012/037320 A2 | 3/2012 |
| WO | 2013020245 A1 | 2/2013 |
| WO | 2013020246 A1 | 2/2013 |
| WO | 2013090664 A1 | 6/2013 |
| WO | 2013090683 A1 | 6/2013 |
| WO | 2014035945 A1 | 3/2014 |
| WO | WO2014/093941 | 6/2014 |
| WO | 2016046786 A1 | 3/2016 |

OTHER PUBLICATIONS

Dolgin Elie: "Long-acting HIV drugs advanced to overcome adherence challenge" Nature Medicine; vol. 20 No. 4, Apr. 2014, pp. 323-324.
Aiken et al., Betulinic acid derivatives as HIV-1 antivirals. Trends Mol Med. Jan. 2005;11(1):31-6.
Azijn et al., TMC278, a next-generation nonnucleoside reverse transcriptase inhibitor (NNRTI), active against wild-type and NNRTI-resistant HIV-1. Antimicrob Agents Chemother. Feb. 2010;54(2):718-27.
Highleyman, ICAAC 2012: Long-acting Integrase inhibitor S/GSK1265744 Active Against HIV Subtypes. Retrieved online: http://www.hivandhepatitis.com/hiv-aids/hiv-aids-topics/hiv-treatment/3781-icaac-2012-long-acting-integrase-inhibitor-sgsk1265744-active-against-multiple-hiv-subtypes. Sep. 2012.
Knapp et al., In vitro selection of clinically relevant bevirimat resistance mutations revealed by "deep" sequencing of serially passaged, quasispecies-containing recombinant HIV-1. J Clin Microbiol. Jan. 2011;49(1):201-8.
Lan et al., 3D-QSAR studies on betulinic acid and betulin derivatives as anti-HIV-1 agents using CoMFA and CoMSIA. Medicinal Chemistry Research. Nov. 2011;20(8):1247-1259.
Lansdon et al., Crystal structures of HIV-1 reverse transcriptase with etravirine (TMC125)and rilpivirine (TMC278): implications for drug design. J Med Chem. May 27, 2010;53(10):4295-9.
The Merck Index. Abacavir. 14th Edition, p. 9 (2013).
Yoshinaga et al., Antiviral Characteristics of S/GSK1265744, An HIV Integrase Inhibitor (INI) Dosed by Oral or Long-acting Parenteral Injection . . . once monthly or 3 months dosing/PrEP/HAART. 52nd ICAAC Interscience Conference on Antimicrobial Agents and Chemotherapy. Sep. 9-12, 2012.
U.S. Appl. No. 13/714,627, filed Dec. 14, 2012 (now U.S. Pat. No. 9,102,685).
U.S. Appl. No. 13/714,627 Non Final dated Jul. 1, 2014.
U.S. Appl. No. 13/714,627 Notice of allowance filed Dec. 2, 2014.
U.S. Appl. No. 13/714,627 Notice of allowance dated Mar. 31, 2015.
U.S. Appl. No. 13/714,627 preliminary amendment filed May 27, 2014.
U.S. Appl. No. 13/714,627 RCE amendment filed Mar. 2, 2015.
U.S. Appl. No. 13/714,627 Response filed Sep. 25, 2014.
U.S. Appl. No. 14/365,802, filed Jun. 16, 2014 Derivatives of Betulin.
U.S. Appl. No. 14/365,802 Non Final dated Jun. 26, 2015.
U.S. Appl. No. 14/365,802 preliminary amendment filed Jun. 16, 2014.
U.S. Appl. No. 14/365,802 Response to Office Action dated Dec. 23, 2015.
U.S. Appl. No. 14/461,731, filed Aug. 18, 2014 Derivatives of Betulin.
U.S. Appl. No. 14/461,731 Final dated May 10, 2016.
U.S. Appl. No. 14/461,731 Issue Fee Payment dated Feb. 28, 2017.
U.S. Appl. No. 14/461,731 Non Final dated Nov. 19, 2015.
U.S. Appl. No. 14/461,731 Notice of allowance dated Dec. 9, 2016.
U.S. Appl. No. 14/461,731 Petition to Withdraw dated Mar. 21, 2017.
U.S. Appl. No. 14/461,731 RCE amendment filed Nov. 10, 2016.
U.S. Appl. No. 14/461,731 Response filed Feb. 19, 2016.
U.S. Appl. No. 14/651,673, filed Jun. 12, 2014 Pharmaceutical Composition.
U.S. Appl. No. 14/651,673 Non Final dated Mar. 24, 2016.
U.S. Appl. No. 14/651,673 Notice of Allowance dated Dec. 13, 2016.
U.S. Appl. No. 14/651,673 Notice of Allowance dated Apr. 11, 2017.
U.S. Appl. No. 14/651,673 Preliminary Amendment filed Jun. 12, 2015.
U.S. Appl. No. 14/651,673 Response filed Sep. 26, 2016.
U.S. Appl. No. 14/651,673 Response to Restriction Requirement dated Mar. 7, 2016.
U.S. Appl. No. 14/651,673 Restriction Requirement dated Jan. 6, 2016.
U.S. Appl. No. 14/651,673 Supplemental Response filed Nov. 28, 2016.
U.S. Appl. No. 14/757,754, filed Dec. 23, 2015 Derivatives of Betulin.
U.S. Appl. No. 14/757,754 Non Final Office Action dated Feb. 1, 2017.
U.S. Appl. No. 14/757,754 Preliminary Amendment filed Dec. 23, 2015.
U.S. Appl. No. 14/757,754 Response filed May 1, 2017.
U.S. Appl. No. 15/464,553, filed Mar. 21, 2017 Derivatives of Betulin.
U.S. Appl. No. 15/464,553, Preliminary Amendment filed Apr. 28, 2017.
U.S. Appl. No. 15/514,564, filed Mar. 27, 2017 Derivatives of Betulin.
U.S. Appl. No. 15/514,564 Preliminary Amendment filed Mar. 27, 2017.
International Search Report and Written Opinion for Application No. PCT/U52012/069637, dated Feb. 19, 2013.

LONG ACTING PHARMACEUTICAL COMPOSITIONS

CROSS REFERENCE TO RELATED PATENTS AND PATENT APPLICATIONS

This application is a 371 of International Application No PCT/IB2015/057360, filed Sep. 24, 2015, which claims the benefit of U.S. Provisional Patent Application No. 62/055,779, filed on Sep. 26, 2014; each of which are hereby incorporated by reference in their entirety.

FIELD OF THE INVENTION

The present invention relates to long acting parenteral (LAP) formulations as well as methods of treating Human Immunodeficiency Virus (HIV) infection and acquired immunodeficiency syndrome (AIDS) using the same.

BACKGROUND OF THE INVENTION

Presently, long-term suppression of viral replication with antiretroviral drugs is the only option for treating HIV-1 infection. To date, a number of approved drugs have been shown to greatly increase patient survival. However, therapeutic regimens known as highly active antiretroviral therapy (HAART) are often complex because a combination of different drugs must be administered to the patient to avoid the rapid emergence of drug-resistant HIV-1 variants. Such regimens typically entail frequent administration of multiple drugs at high doses to maintain efficacious drug plasma levels. Consequently, a prescribed treatment may require ingestion of multiple and/or large dosage forms which can lead to reduced patient compliance resulting in reduced drug efficacy and development of multiple drug resistant strains of HIV. Therefore, despite the positive impact of HAART on patient survival, drug effectiveness and resistance issues can still occur with sometimes fatal consequence.

The emergence of multidrug-resistant (MDR) HIV-1 isolates has serious clinical consequences and must be suppressed with a new drug regimen, known as salvage therapy. Current guidelines recommend that salvage therapy includes at least two, and preferably three, fully active drugs. Typically, first-line therapies combine three to four drugs targeting the viral enzymes reverse transcriptase (RT) and protease (PR). One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase (IN) inhibitors. However, resistance to all three new drug classes has already been reported both in vitro and in vivo.

Accordingly, successful treatments of HIV-1-infected patients which alleviate compliance issues and are effective against resistant strains are a continual need.

SUMMARY OF THE INVENTION

The present invention addresses the issue of non-compliance as well as the prevention of, or treatment of, HIV by formulating certain HIV inhibitor compounds, including the first compound, second compound, and/or third compound, as a Long Acting Parenteral (LAP) composition suitable for administration, for example, once per month, once every 2 months, once every 3 months, once every 6 months or once every 12 months.

For example, a LAP composition of the present invention may comprise a pharmaceutically acceptable excipient and a first compound of the structure:

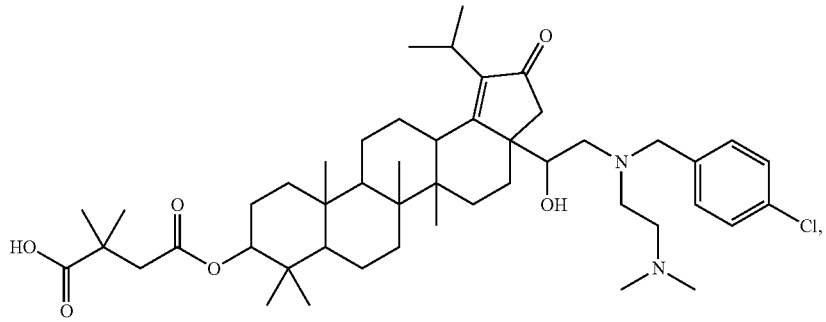

("first compound") or a pharmaceutically acceptable salt thereof,
in combination with:
a second compound ("second compound") of the structure:

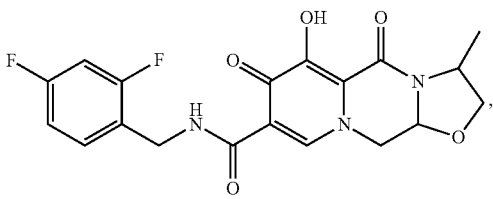 [SMILES: CC1COC2Cn3cc(C(=O)NCc4ccc(F)cc4F)c(=O)c(O)c3C(=O)N12]

or a pharmaceutically acceptable salt thereof, and optionally, also in combination with
a third compound ("third compound") of the structure:

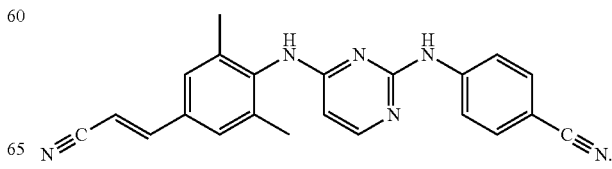

In other embodiments, the first compound and second compound may comprise their isomer forms wherein the present invention provides a long acting parenteral (LAP) pharmaceutical composition comprising a pharmaceutically acceptable excipient and a first compound of the structure:

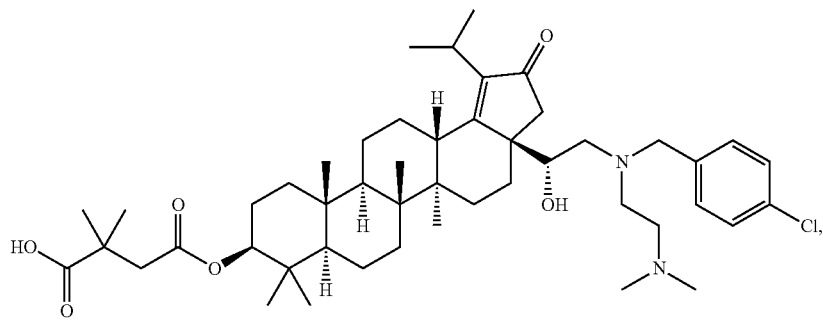

or a pharmaceutically acceptable salt thereof, in combination with a second compound of the structure:

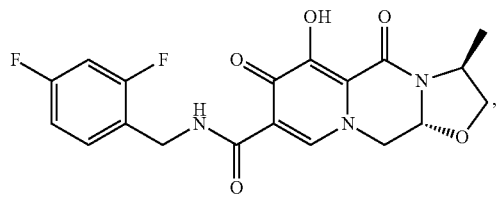

or a pharmaceutically acceptable salt thereof.

In one aspect of the present invention, there is provided a LAP pharmaceutical composition including the first compound, second compound, and/or third compound, or a pharmaceutically acceptable salt thereof.

In a second aspect of the present invention, there is provided a method for the treatment or prevention of an HIV infection in a human having an HIV infection including administering to the human a LAP pharmaceutical composition including the first compound, second compound, and/or third compound, or a pharmaceutically acceptable salt thereof.

In a third aspect of the present invention, there is provided a method for the treatment or prevention of an HIV infection in a human having an HIV infection including administering to the human a LAP pharmaceutical composition including the first compound, second compound, and/or third compound, or a pharmaceutically acceptable salt thereof.

In a fourth aspect of the present invention, there is provided use of a LAP pharmaceutical composition including the first compound, second compound, and/or third compound, or a pharmaceutically acceptable salt thereof in HIV medical therapy.

In a fifth aspect of the present invention, there is provided the use of the first compound, second compound, and/or third compound, or a pharmaceutically acceptable salt thereof in the preparation of a long acting parenteral medicament for use in the treatment or prevention of HIV infection in a human.

In an sixth aspect of the present invention, there is provided the use of the first compound, second compound, and/or third compound, or a pharmaceutically acceptable salt thereof in the preparation of a long acting parenteral medicament for use in the treatment or prevention of HIV infection in a human.

DETAILED DESCRIPTION OF THE INVENTION

Figure 1:
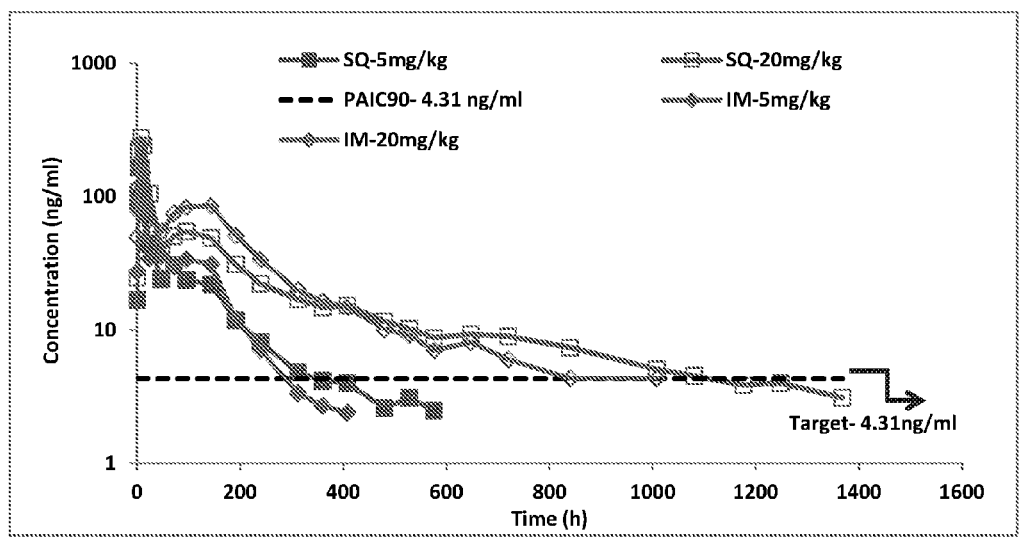
FIG. 1 depicts a plot of LAP Mean Concentration of the first compound versus time in hours of a LAP Rat PK study at 5 mg/kg and 20 mg/kg doses.

The HIV Gag polyprotein precursor (Pr55Gag), which is composed of four protein domains—matrix (MA), capsid (CA), nucleocapsid (NC) and p6—and two spacer peptides, SP1 and SP2, represents a new therapeutic target. Although the cleavage of the Gag polyprotein plays a central role in the progression of infectious virus particle production, to date, no antiretroviral drug has been approved for this mechanism.

In most cell types, assembly occurs at the plasma membrane, and the MA domain of Gag mediates membrane binding. Assembly is completed by budding of the immature particle from the cell. Concomitant with particle release, the virally encoded PR cleaves Gag into the four mature protein domains, MA, CA, NC and p6, and the two spacer peptides, SP1 and SP2. Gag-Pol is also cleaved by PR, liberating the viral enzymes PR, RT and IN. Gag proteolytic processing induces a morphological rearrangement within the particle, known as maturation. Maturation converts the immature, donut-shaped particle to the mature virion, which contains a condensed conical core composed of a CA shell surrounding the viral RNA genome in a complex with NC and the viral enzymes RT and IN. Maturation prepares the virus for infection of a new cell and is absolutely essential for particle infectivity.

Bevirimat (PA-457) is a maturation inhibitor that inhibits the final step in the processing of Gag, the conversion of capsid-SP1 (p25) to capsid, which is required for the formation of infectious viral particles. Bevirimat has activity against ART-resistant and wild-type HIV, and has shown synergy with antiretrovirals from all classes. Bevirimat reduced HIV viral load by a mean of 1.3 $\log_{10}$/mL in patients who achieved trough levels of >=20 μg/mL and who did not have any of the key baseline Gag polymorphisms at Q369, V370 or T371. However, Bevirimat users with Gag polymorphisms at Q369, V370 or T371 demonstrated significantly lower load reductions than patients without Gag polymorphisms at these sites.

Other examples of maturation inhibitors can be found in PCT Patent Application No. WO2011/100308, "Derivatives of Betulin"; PCT Patent Application No. PCT/US2012/024288, "Novel Anti-HIV Compounds and Methods of Use Thereof"; Chinese PCT Application No. PCT/CN2011/001302, "Carbonyl Derivatives of Betulin"; Chinese PCT Application No. PCT/CN2011/001303, "Methylene Derivatives of Betulin"; Chinese PCT Application Nos. PCT/CN2011/002105 and PCT/CN2011/002159, "Propenoate Derivatives of Betulin"; and U.S. Provisional Application No. 61/576,448, "Derivatives of Betulin". With each iteration of maturation inhibitor a need exists to optimize the polymorphism isolate coverage and achieve maximum potency while minimizing the protein shift. To date, no maturation inhibitor has achieved an optimal balance of these three properties.

PCT Published Application No. WO2013090664, which is hereby incorporated by reference in its entirety, and deriving from U.S. Provisional Application 61/576,448, filed Dec. 16, 2011, discloses maturation inhibitors which are betulin derivatives useful in the treatment of HIV infection and AIDS. Such betulin derivatives include 4-(((3aR,5aR,5bR,7aR,9S,11aR,11bR,13aS)-3a-((R)-2-((4-Chlorobenzyl)(2-(dimethylamino) ethyl)amino)-1-hydroxyethyl)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy)-2,2-dimethyl-4-oxobutanoic acid which is the "First Compound":

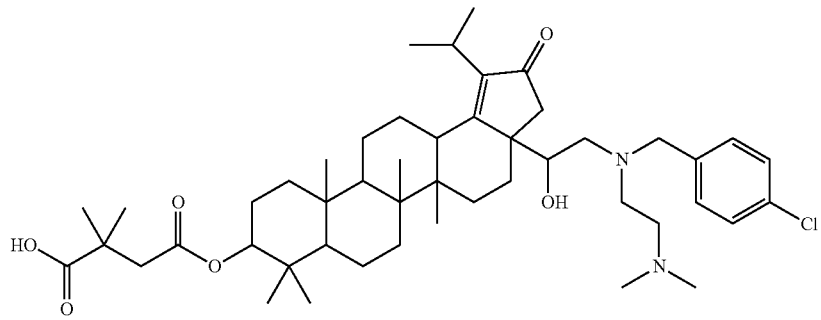

is a maturation inhibitor believed to provide optimization of the polymorphism isolate coverage which achieves maximum potency while minimizing the protein shift. This compound is currently being developed for the treatment of HIV infection and associated disease states.

The "second compound" is Cabotegravir, an HIV integrase inhibitor currently in development by GlaxoSmithKline as a long acting parenteral drug. The second compound has the following structure:

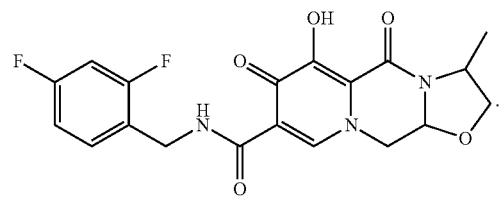 [SMILES: CC1COC2Cn3cc(C(=O)NCc4ccc(F)cc4F)c(=O)c(O)c3C(=O)N12]

One of skill will understand how to make cabotegravir from the following published PCT applications: PCT Patent Application No. PCT/US2006/016604 and PCT Patent Application No. PCT/US2011/051713, both of which are hereby incorporated by reference in their entireties.

The "third compound" is Rilpivirine, 4-[[4-[[4-(2-Cyanoethenyl)-2,6-dimethylphenyl]amino]-2-pyrimidinyl]amino]benzonitrile, which is a non-nucleoside reverse transcriptase inhibitor (NNRTI) of human immunodeficiency virus type 1 (HIV-1) and indicated for the treatment of HIV-1 infection in treatment-naive adult patients in combination with other antiretroviral agents. Rilpivirine hydrochloride was launched as film coated tablets in Europe and the US (brand name Edurant). One of skill in the art will understand how to make Rilpivirine from one or more of the following U.S. Pat. Nos. 6,838,464, 7,067,522, 7,125,879, 7,638,522, 8,080,551, and 8,101,629, all of which are hereby incorporated by reference in their entireties. Rilpivirine (i.e., the third compound) has the following structure:

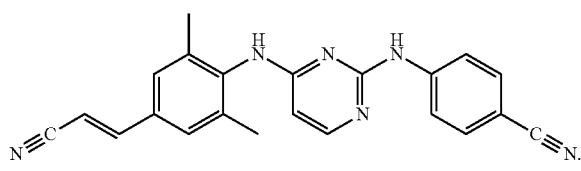 [SMILES: Cc1cc(/C=C/C#N)cc(C)c1Nc1ccnc(Nc2ccc(C#N)cc2)n1]

In spite of major progress made in the past decade to inhibit the replication of HIV-1, thereby preventing the clinical presentation of AIDS, none of the currently available treatments for HIV infection can cure the infection. Also HAART, or highly active antiretroviral therapy consisting of at least three antiretroviral drugs, may fail following the development of viral resistance. Factors contributing to the incomplete suppression of HIV and to the development of resistance include insufficient drug potency, non-compliance, restricted tissue penetration, drug resistance and several host factors, such as host genetics. Thus, compliance during a life-long treatment is crucial, as establishing minimal inhibitory drug concentrations in the blood inhibits viral growth and the development of resistant strains.

The present invention addresses such problematic issues in the treatment or prevention of HIV by formulating the first compound, second compound, and the optional third compound either each one separately or two or three of them together as a long-acting parenteral (LAP) composition or depot formulation suitable for administration, for example, once per week, once every two weeks, once per month, once every 2 months, once every 3 months, once every 6 months or once every 12 months.

Long-acting parenteral formulations of the first and second compound and optional third compound could generate sustained effective inhibitory concentrations with infrequent dosing and may improve adherence to therapy. Next to facilitating maintenance of viral suppression following traditional anti-HIV therapy, a long-acting formulation, may also serve as a practical opportunity for pre-exposure prophylaxis.

The present invention features pharmaceutical compositions comprising an active ingredient which is the first and second compound and optional third compound, or pharmaceutically acceptable salts thereof, suitable for administration once monthly or longer.

Further features of the present invention are methods of using these pharmaceutical compositions.

In one embodiment, the present invention features pharmaceutical compositions, comprising the first compound, second compound, and/or third compound, or pharmaceutically acceptable salt thereof, and a surfactant system.

In other embodiments, the present invention features a pharmaceutical composition, comprising a therapeutically effective amount of first and second compound and optional third compound, or pharmaceutically acceptable salts thereof, and a surfactant system.

Pharmaceutically acceptable salts include, but are not limited to those described in PCT Published Application No. WO2013090664 deriving from U.S. Provisional Application 61/576,448, filed Dec. 16, 2011.

The term "therapeutically effective amount," as used herein, means a sufficient amount of a drug, compound, composition, product or pharmaceutical agent to abate or reverse or treat a malady in a human or other mammal.

The present invention features parenteral pharmaceutical compositions for administration to a subject, for example a human.

In another embodiment, the present invention features long-acting parenteral pharmaceutical compositions comprising the first and second compound and optional third compound, or pharmaceutically acceptable salts thereof, and a surfactant system for weekly (once every week) administration.

In another embodiment, the present invention features long-acting parenteral pharmaceutical compositions comprising the first and second compound and optional third compound, or a pharmaceutically acceptable salt thereof, and a surfactant system for bi-weekly (once every two weeks) administration.

In another embodiment, the present invention features long-acting parenteral pharmaceutical compositions comprising the first and second compound and optional third compound, or a pharmaceutically acceptable salt thereof, and a surfactant system for once monthly administration.

In another embodiment, the present invention features long-acting parenteral pharmaceutical compositions comprising the first and second compound and optional third compound, or a pharmaceutically acceptable salt thereof, and a surfactant system for bi-monthly (once every two months) administration.

In another embodiment, the present invention features long-acting parenteral pharmaceutical compositions comprising the first and second compound and optional third compound, or a pharmaceutically acceptable salt thereof, and a surfactant system for tri-monthly (once every three months) administration.

In another embodiment, the present invention features long-acting parenteral pharmaceutical compositions comprising the first and second compound and optional third compound, or a pharmaceutically acceptable salt thereof, and a surfactant system administration once every six or twelve months, or any time point within this range.

The compositions of the present invention provide for the slow release of the first and second compound and optional third compound, over an extended period of time within the body of a subject. Therefore, in order to achieve therapeutic levels of drug, the first and second compound and optional third compound, advantageously is released from the composition within approximately one to three months, or any time point within this range.

An embodiment of the present invention is a pharmaceutical composition suitable for parenteral administration comprising the first and second compound and optional third compound, and a surfactant system comprising a combination of polymers providing for the release of the first and second compound and optional third compound, over a period of one week to three months. A suitable combination of polymers is, for example, polysorbate 80 and polyvinylpyrrolidone (PVP).

The compositions of the present invention may be administered to the subject by various routes, including intramuscular (IM), intravenous (IV), or subcutaneous (SQ). Therefore, in one embodiment, the compositions of the present invention are administered to a subject by an intramuscular route. In another embodiment, the compositions of the present invention are administered to a subject by an intravenous route. In another embodiment, the compositions of the present invention are administered to a subject by a subcutaneous route.

For purposes of the present invention, a "surfactant system" means any formulation suitable for pharmaceutical purposes that includes at least one surfactant. For example, a surfactant system that can be used with the present invention may include, in addition to a surfactant, additional components such as buffers, polymers (for drug particles), wetting agents, stabilizers, tonicity modifiers, and solvents such as water.

The surfactant system may include any surfactant as long as it is compatible with pharmaceutical applications. For example, suitable surfactants include, but are not limited to, polyoxyethylene sorbitan fatty acid esters (polysorbates such as polysorbate 20 or 80), poloxamers (such as LUTROL™ F68, F108 and F127 which are block copolymers of ethylene oxide and propylene oxide, sodium dodecylsulfate and/or sodium lauryl sulphate), sorbitan esters of fatty acids (SPAN), polyethoxylated castor oil and its derivatives, tocopheryl polyethylene glycol succinate, and polyvinyl alcohols. In certain embodiments, the surfactant system comprises an amount of surfactant that ranges from about 0.01% (w/v) to about 5% (w/v) surfactant. In other embodiments, the surfactant system comprises an amount of surfactant that ranges from about 0.1% (w/v) to about 3% (w/v) surfactant. In still other embodiments, the surfactant system comprises about 0.2% (w/v) surfactant. In still other embodiments, the surfactant system comprises about 0.4% (w/v) surfactant. In other embodiments, the surfactant system comprises polysorbate-80 (e.g., Tween-80). In still other embodiments, the surfactant system comprises 0.4% (w/v) polysorbate-80.

Representative stabilizers include, but are not limited to, polyethylene glycols, carboxymethylcellulose calcium, carboxymethylcellulose sodium, methylcellulose, hydroxyethylcellulose, hydroxypropylcellulose, hydroxymethylpropylcellulose, polysaccharides, hyaluronic acid, polyvinyl alcohol (PVA) and polyvinylpyrrolidone (PVP). In certain embodiments, the surfactant system comprises an amount of stabilizer that ranges from about 0.01% (w/v) to about 5% (w/v) stabilizer. In other embodiments, the surfactant system comprises an amount of stabilizer that ranges from about 1% (w/v) to about 5% (w/v) stabilizer. In other embodiments, the surfactant system comprises an amount of stabilizer that ranges from about 1% (w/v) to about 3% (w/v) stabilizer. In still other embodiments, the surfactant system comprises about 2% (w/v) stabilizer. In other embodiments, the surfactant system comprises polyethylene glycols. In other embodiments, the surfactant system comprises PEG-3350. In still other embodiments, the surfactant system comprises 2% (w/v) PEG-3350.

Suitable buffer salts include, but are not limited to, buffer salts selected from phosphate salts, citrate salts, acetate salts, and tartrate salts, etc. In certain embodiments, the surfactant system comprises an amount of buffer salts that ranges from about 1 mM to about 100 mM buffer salt. In other embodiments, the surfactant system comprises an amount of buffer salts that ranges from about 2 mM to about 50 mM buffer salt. In other embodiments, the surfactant system comprises an amount of buffer salts that ranges from about 3 mM to about 25 mM buffer salt. In other embodiments, the surfactant system comprises an amount of buffer salts that ranges from about 5 mM to about 15 mM buffer salt. In still other embodiments, the surfactant system comprises about 10 mM buffer salt. In certain embodiments, the pH of the buffer salt is adjusted to range from about pH 6.0 to about pH 8.0. In other embodiments, the pH of the buffer salt is adjusted to range from about pH 6.5 to about pH 7.5. In other embodiments, the pH of the buffer salt is adjusted to range from about pH 6.7 to about pH 7.3. In one embodiment, the buffer salt comprises phosphate buffered saline (PBS). In another embodiment, the buffer salt comprises phosphate buffered saline at a concentration of about 10 mM. In another embodiment, the buffer salt comprises phosphate buffered saline at a concentration of about 10 mM and a pH of about 6.9.

Suitable tonicity modifiers include, but are not limited to, sodium chloride, mannitol, sucrose, maltose, and dextrose, etc. In one embodiment, the tonicity modifier comprises sodium chloride. In another embodiment, the tonicity modifier is sodium chloride. In certain embodiments, the surfactant system comprises a concentration of tonicity modifier that ranges from about 0 to about 350 mM. In certain embodiments, the surfactant system comprises a concentration of tonicity modifier that ranges from about 0 to about 175 mM. In certain embodiments, the surfactant system has a tonicity that ranges from about 250 to about 350 mOsmol/kg.

In one embodiment, the first and second compound and optional third compound can be suspended as microparticles in a surfactant system and aqueous buffer. In some embodiments, the first compound can be in an amorphous form or in a crystalline form. Typically, the drug particle size ($D_{50}$) will range from about 0.05 µm to about 100 µm. In other embodiments, the drug particle size will range from about 0.1 µm to about 50 µm. In other embodiments, the drug particle size will range from about 0.1 µm to about 20 µm. In other embodiments, the drug particle size ($D_{50}$) will range from about 0.1 µm to about 10 µm. In other embodiments, the drug particle size ($D_{50}$) will range from about 0.1 µm to about 5 µm. In other embodiments, the drug particle size ($D_{50}$) will range from about 1 µm to about 5 µm. In other embodiments, the drug particle size ($D_{50}$) will range from about 0.05 µm to about 0.05 µm. In other embodiments, the drug particle size ($D_{50}$) will range from about 0.5 µm to about 5 µm. In other embodiments, the drug particle size ($D_{50}$) will range from about 5 µm to about 25 µm. In other embodiments, the drug particle size ($D_{50}$) will range from about 25 µm to about 100 µm.

In still other embodiments, the drug particle size in the surfactant system can be mixed sizes. For example, having substantially different particle sizes from relatively large to relatively small, can achieve acceptable pharmacokinetic parameters for the formulation because the small particles are absorbed and metabolized quicker than the larger particles. This type of mixed particle size formulation could enhance the long acting nature of the present invention by providing a quicker release of drug to the subject early after administration while still maintaining a long acting release of the drug at distant times after administration. Therefore, in one embodiment, the present LAP invention could comprise two or more substantially different particle sizes that would allow for earlier and later release of the first compound and second compound and optional third compound and such differing absorption kinetics would be a means of enhancing a durable long acting drug exposure. In one embodiment, the first compound is in a microparticle form, wherein the microparticles of the first compound range in size from about 0.05 µm to about 100 µm, wherein said microparticles comprise two or more substantially different particle sizes.

In still other embodiments, the drug particles of the first and second compound and optional third compound are encapsulated into polymer based microparticles that can, optionally, be subsequently freeze dried for extended storage. When the term "encapsulated" is used with regards to the present invention, it is meant that the first and second compound and optional third compound is substantially surrounded by a polymer even though some compound may still be present on the surface of the encapsulated compound/polymer structure. Immediately before use, the dry microparticles can optionally suspended in an aqueous buffer solution. The polymers used to prepare such microparticles can be selected from a series of biodegradable polymers including poly (lactic-co-glycolic) acid ($M_w$ 5-200 kD) and its derivatives, such as polyethylene glycol based amphiphilic polymers, etc. The microparticle size ($D_{50}$) could range from about 1 µm to about 100 µm and the drug encapsulation could range from about 10% to about 70% (w/w). In one embodiment, the drug particles of the first and second compound and optional third compound are encapsulated into polymer based microparticles such as those containing RESOMER™ biodegradable polymer. In another embodiment, the drug particles of the first and second compound and optional third compound are encapsulated into polymer based microparticles such as those containing RESOMER™ biodegradable polymer 752S.

In other embodiments, in-situ gels could be used to encapsulate the first compound. This could be a water-miscible organic solvent-based solution that contains both the first compound and a gel-forming polymer that is water-insoluble. Once administrated (IM or SC), the organic solvent dissipates away and the water-insoluble polymer precipitates out to form the gel containing the first compound. The first compound would then slowly diffuse out as the polymer-based gel degrades in body. The polymers used to prepare in-situ gels are selected from a series biodegradable polymers including poly (lactic-co-glycolic) acid ($M_w$ 5-200 kD) and its derivatives, polyethylene glycol based amphiphilic polymers, etc. The organic solvents are selected from N-methyl pyrrolidone (NMP), dimethylsulfoxide (DMSO), dimethylformamide (DMF), dimethylacetamie (DMA), etc. The concentration of the polymer in the organic solvent could be between 1-50% (w/w) and the first compound concentration could be between 1-50% (w/w).

Alternatively, the microparticle formulation can be made through spray-drying process. Similarly, the organic solution containing both the first compound and the selected polymer prepared as described herein is subjected to a spray-drying process where the organic solvent is rapidly evaporated under nitrogen gas flow to form the first and second compound and optional third compound encapsulated microparticles. The drying temperature is no less than 35 C and the solution spray rate is no less than 0.1 ml/min. For the in-situ gel microparticles, the first compound and the selected polymer could be co-dissolved into the suitable organic solvent wherein the organic solvent must meet the following criteria: a) has a good solubility for the selected polymer; b) has a good miscibility with aqueous solution; and c) has a low toxicity and demonstrated safety when use in human; for example N-methyl pyrrolidone (NMP), dimethylsulfoxide (DMSO), dimethylformamide (DMF), dimethylacetamie (DMA), etc. The resulted solution containing both the first compound and selected polymer can be formulated by varying the polymer concentration, the polymer to the first compound ratio in the solvent so as to control the gel forming rate after administration and the subsequent drug diffusion rate. The solution finally is subjected to a terminal sterilization by γ-irradiation on dry ice at a minimum dose of 25 kGy.

An example of a combination of polymers includes a polysorbate, for example, polysorbate 80 as wetting agent and a polyvinylpyrrolidone (PVP), for example, Plasdone K29/32 as a stabilizer. Therefore, in one embodiment, the present invention features a parenteral pharmaceutical composition comprising a first and second compound and optional third compound, or pharmaceutically acceptable salts thereof, and polysorbate 80 and the polyvinylpyrrolidone: Plasdone K29/32.

An embodiment of the present invention is a pharmaceutical composition for parenteral administration comprising the first and second compound and optional third compound, and a surfactant system suitable for commonly known sterilization technologies such as gamma irradiation, electron beam irradiation and autoclave sterilization.

An embodiment of the present invention is a pharmaceutical composition for parenteral administration comprising the first and second compound and optional third compound, and a surfactant system that can be manufactured using aseptic technique.

An embodiment of the present invention is a pharmaceutical composition for parenteral administration comprising the first and second compound and optional third compound, and a surfactant system suitable for gamma radiation sterilization.

An embodiment of the present invention is a pharmaceutical composition for parenteral administration comprising the first and second compound and optional third compound, and a surfactant system suitable for sterilization technologies by electron beam irradiation or autoclave sterilization.

An embodiment of the present invention is a pharmaceutical composition for parenteral administration that can be presented as a "ready to use" sterile suspension or lyophile for reconstitution.

The compositions of the present invention may be administered by subcutaneous or intramuscular injection. The compositions of the present invention may also be administered by intradermal or intravitreal injection or implant. The compositions of the present invention may also be administered by other parenteral routes of administration.

The preparation of the compositions of the present invention may be performed by milling using a wet bead mill and sterilized by gamma irradiation.

Another feature of the present invention is to simplify treatment regimens for HIV with the goal of enhancing patient compliance by providing a simplified dosage form containing therapeutically effective amounts of the first and second compound and optional third compound, or a pharmaceutically acceptable salt thereof.

The present invention also features a method for treating HIV infections in a human, which method comprises administering to said human a composition according to the invention. The present invention features the use of a pharmaceutical composition according to the invention in the treatment of HIV infections. The present invention features the manufacture of a medicament according to the invention for use in medical therapy. The present invention features the manufacture of a medicament according to the invention for use in the treatment of HIV infection.

The present invention also features a method for treating HIV infections in a human which method comprises administering to said human a composition according to the invention before, during, or after therapy with the first and second compound and optional third compound, in tablet or solution form.

It will be appreciated by those skilled in the art that reference herein to "treatment" extends to treatment of an established malady, infection or symptoms thereof.

The present invention also features a method for preventing HIV infections in a human, which method comprises administering to said human a composition according to the invention. The present invention features the use of a pharmaceutical composition according to the invention in the prevention of HIV infections. The present invention features the manufacture of a medicament according to the invention for use in prophylactic medical therapy. The present invention features the manufacture of a medicament according to the invention for use in preventing HIV infection.

The present invention also features a method for treating or preventing HIV infections in a human which method comprises administering to said human a composition according to the invention before, during, or after therapy with the first and second compound and optional third compound, in tablet or solution form.

Therefore, in certain embodiments of the present invention, there is provided a pharmaceutical composition comprising a therapeutically effective amount of a long acting formulation comprising a first compound of the structure:

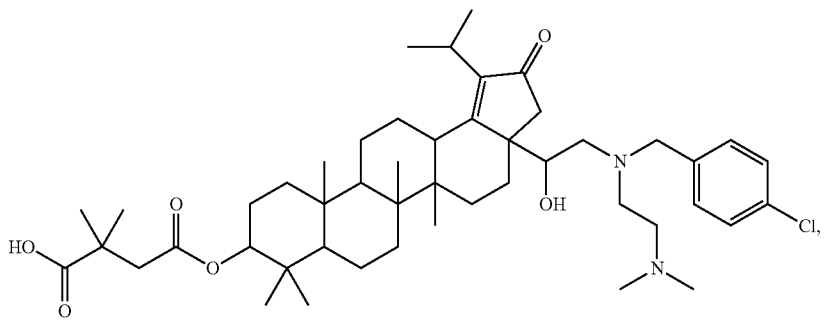

("first compound") or a pharmaceutically acceptable salt thereof,
in combination with:
a second compound ("second compound") of the structure:

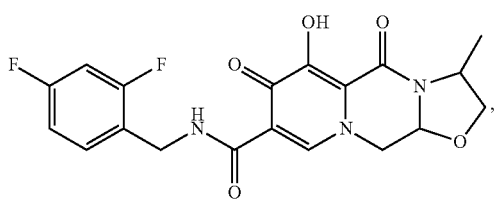 [SMILES: CC1COC2Cn3cc(C(=O)NCc4ccc(F)cc4F)c(=O)c(O)c3C(=O)N12]

or a pharmaceutically acceptable salt thereof, and optionally in combination with
a third compound ("third compound") of the structure:

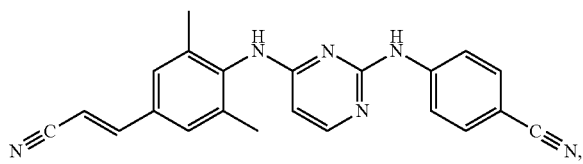 [SMILES: Cc1cc(/C=C/C#N)cc(C)c1Nc1ccnc(Nc2ccc(C#N)cc2)n1]

in a pharmaceutically acceptable carrier for parenteral administration.

In other embodiments, there is provided a pharmaceutical composition comprising the first and second compound and optional third compound, which are formulated for subcutaneous administration.

In other embodiments, there is provided a pharmaceutical composition comprising the first and second compound and optional third compound, which are formulated for intramuscular administration.

In other embodiments, there is provided a pharmaceutical composition comprising the first and second compound and optional third compound, which are formulated for administration once weekly or longer.

In other embodiments, there is provided a pharmaceutical composition comprising the first and second compound and optional third compound, which are formulated for administration once weekly.

In other embodiments, there is provided a pharmaceutical composition comprising the first and second compound and optional third compound, which are formulated for administration once per month.

In other embodiments, there is provided a pharmaceutical composition comprising the first and second compound and optional third compound, which are formulated for administration once every two months. In other embodiments, there is provided a pharmaceutical composition comprising the first and second compound and optional third compound, which are formulated for administration once every three months. In other embodiments, there is provided a pharmaceutical composition comprising the first and second compound and optional third compound, which are formulated for administration at any interval between 30 and 365 days.

In other embodiments, there is provided a pharmaceutical composition comprising the first compound and second compound and optional third compound, wherein the compounds are present in the composition in the form of crystalline nanoparticles.

In other embodiments, there is provided a pharmaceutical composition comprising the first compound and second compound and optional third compound, wherein the compounds are present in the composition in the form of matrix release particles.

In other embodiments, there is provided a pharmaceutical composition comprising the first compound and second compound and optional third compound, wherein the composition can be terminally sterilized by gamma irradiation.

In other embodiments, there is provided a method for the treatment of an HIV infection in a human having an HIV infection comprising administering to the human a single treatment pharmaceutical composition comprising a therapeutically effective amount of a long acting formulation comprising the first and second compound and optional third compound, or pharmaceutically acceptable salts thereof, in a pharmaceutically acceptable carrier for parenteral administration.

In other embodiments, there is provided a method for the prevention of an HIV infection in a human comprising administering to a human at risk of acquiring an HIV infection, a single treatment pharmaceutical composition comprising a therapeutically effective amount of a long acting formulation comprising the first compound and second compound and optional third compound, or pharmaceutically acceptable salts thereof, in a pharmaceutically acceptable carrier for parenteral administration.

In other embodiments, there is provided a LAP pharmaceutical composition, comprising: the first compound, second compound, and/or third compound, or pharmaceutically acceptable salts thereof.

In other embodiments, there is provided a method for the treatment of an HIV infection in a human having an HIV infection, comprising: administering to the human a LAP pharmaceutical composition including the first compound, second compound, and/or third compound, or pharmaceutically acceptable salts thereof.

In other embodiments, there is provided a method for the prevention of an HIV infection in a human having an HIV infection, comprising: administering to the human a LAP pharmaceutical composition including the first compound, second compound, and/or third compound, or pharmaceutically acceptable salts thereof.

In other embodiments, there is provided a LAP pharmaceutical composition, comprising: the first compound and second compound and/or third compound, or pharmaceutically acceptable salts thereof and, further comprising a surfactant system.

In other embodiments, there is provided a LAP pharmaceutical composition, comprising: the first compound and second compound and/or optional third compound or a pharmaceutically acceptable salt thereof, further comprising a surfactant system, wherein the surfactant system comprises a surfactant in an amount ranging from about 0.1% (w/v) to about 3% (w/v) surfactant, or an amount ranging from 0.2% (w/v) to about 0.4% (w/v) surfactant, or the surfactant system comprises about 0.4% (w/v) surfactant.

In other embodiments, there is provided a LAP pharmaceutical composition, comprising: the first compound and second compound and/or optional third compound in combination with one or more additional compounds selected from the group consisting of dolutegravir and ritonavir, or a pharmaceutically acceptable salt thereof.

In other embodiments, there is provided a method for the treatment of an HIV infection in a human having an HIV infection, comprising: administering to the human a LAP pharmaceutical composition including the first compound and second compound and/or optional third compound, or pharmaceutically acceptable salts thereof, in combination with one or more additional compounds selected from the group consisting of dolutegravir and ritonavir, or a pharmaceutically acceptable salt thereof.

In other embodiments, there is provided a LAP pharmaceutical composition, comprising: the first compound and second compound and/or optional third compound, or pharmaceutically acceptable salts thereof, in combination with any boosting agent, such as, ritonavir. The boosting agent could be dosed simultaneously as the first compound in the same IV or SC syringe, or it could be dosed separately as an oral tablet or capsule.

In other embodiments, the LAP composition comprising the first compound and second compound and/or optional third compound are administered to the subject only after the subject has been administered treatment comprising a generally accepted antiretroviral (ARV) regimen. An initial ARV regimen generally consists of two NRTIs in combination with an NNRTI, a PI (preferably boosted with ritonavir [RTV]), an INSTI, or a CCR5 antagonist (namely maraviroc [MVC]). In clinical trials, NNRTI-, PI-, INSTI-, or CCR5 antagonist-based regimens have all resulted in HIV RNA decreases and CD4 cell increases in a large majority of patients. For example, one generally accepted ARV regimen comprises could be selected from any of the following for antiretroviral (ARV)-naive patients:
efavirenz/tenofovir disoproxil fumarate/emtricitabine (EFV/TDF/FTC)
ritonavir-boosted atazanavir+tenofovir disoproxil fumarate/emtricitabine (ATV/r+TDF/FTC)
ritonavir-boosted darunavir+tenofovir disoproxil fumarate/emtricitabine (DRV/r+TDF/FTC)
raltegravir+tenofovir disoproxil fumarate/emtricitabine (RAL+TDF/FTC)

The pharmaceutical compositions of the invention are presented as pharmaceutical compositions suitable for parenteral administration. The compositions may also include a safe and effective amount of other active ingredients, such as antimicrobial agents, antiviral agents, or preservatives.

It will be appreciated by those skilled in the art that the amount of active ingredients required for use in treatment will vary according to a variety of factors, including the nature of the condition being treated and the age and condition of the patient, and will ultimately be at the discretion of the attending physician, veterinarian or health care practitioner.

Compositions of the present invention enable patients greater freedom from multiple dosage regimens and ease the needed diligence required in remembering complex daily dosing times and schedules. The compositions of the present invention are particularly suitable for administration as a single dose monthly, bi-monthly or tri-monthly, or at any interval between 30 and 365 days, including every six or twelve months.

Advantageously, the compositions of the present invention may be administered once per month.

The compositions of the present invention may be used in combination with other pharmaceutical formulations as a component of a multiple drug treatment regimen. Such combinations could be administered to a subject in one dosage unit, such as a fixed dose combination or it could be administered in separate dosage units.

Compositions of the present invention may also be packaged as articles of manufacture comprising a therapeutically effective amount of a compound of formula (I), or a pharmaceutically acceptable salt thereof; and therapeutically effective amount of one or more of the following: nucleoside reverse transcriptase inhibitor, non-nucleoside reverse transcriptase inhibitor, protease inhibitor, and integrase inhibitor.

The packaging material may also have labelling and information related to the pharmaceutical composition printed thereon. Additionally, an article of manufacture may contain a brochure, report, notice, pamphlet, or leaflet containing product information. This form of pharmaceutical information is referred to in the pharmaceutical industry as a "package insert." A package insert may be attached to or included with a pharmaceutical article of manufacture. The package insert and any article of manufacture labelling provides information relating to the pharmaceutical composition. The information and labelling provides various forms of information utilized by health-care professionals and patients, describing the composition, its dosage and various other parameters required by regulatory agencies such as the United States Food and Drug Agencies.

The present invention further provides the following embodiments:
  (a) A parenteral pharmaceutical composition comprising an effective amount of the first and second compounds and/or optional third compound, or pharmaceutically acceptable salts thereof, for the long term treatment of HIV infection, or prevention of HIV infection in an individual at risk of being infected by HIV, wherein the composition is administered intermittently at a time interval of at least one week.
  (b) The composition according to (a) wherein the composition is administered once every two weeks.
  (c) The composition according to (a) wherein the composition is administered once every month.
  (d) The composition according to any one of (a) to (c) wherein the effective amount of each of the first and second compounds and/or optional third compound, or pharmaceutically acceptable salts thereof, is selected such that the blood plasma concentration of the first and second compounds and/or optional third compound, in a subject is kept during a prolonged period of time at a level between a maximum blood plasma level which is the blood plasma level that causes significant side effects and the minimum blood plasma level that is the lowest blood plasma level that causes the first and second compound and optional third compound, to provide effective treatment or prevention of HIV infection.

(e) The composition according to (d) wherein the blood plasma level of a subject is kept at a level equal to or above about 150 ng/ml, in particular equal to or above about 600 ng/ml.

(f) The composition according to any one of (a) to (e), wherein the composition is administered subcutaneously or intramuscularly.

(g) The composition according to any one of (a) to (f), which comprises the aforementioned surfactant system comprising polysorbate and /or polyvinylpyrrolidone.

(h) A method for the treatment or prevention of an HIV infection in a human comprising a pharmaceutical composition according to any of the above (a) to (g).

The dose of the administered first and second compound and optional third compound, which is the amount of the compounds in the parenteral composition for use in the invention, may be selected such that the blood plasma concentration of the compounds in a subject is kept during a prolonged period of time above a minimum blood plasma level. The term "minimum blood plasma level" (or $C_{min}$) in this context refers to the lowest efficacious blood plasma level, that is, the blood plasma level of the compounds that provides effective prevention or treatment HIV infection. In the case of transmission of HIV from an individual infected by HIV to an individual not infected by HIV, this is the lowest blood plasma level that is effective in inhibiting said transmission.

The blood plasma level of the LAP formulations comprising the first and second compounds and optional third compound in a subject may be kept at a level above a minimum blood plasma level of about 170 ng/ml, about 700 ng/ml, or about 1000 ng/ml. The blood plasma levels of the compounds in a subject may be kept above these minimum blood plasma levels because at lower levels the drug may no longer be effective, thereby increasing the risk of transmission of HIV infection, and may be suboptimal for treatment of HIV infected subjects. Plasma levels of the compounds may be kept at higher levels to avoid the development of HIV mutations, while maintaining a safety margin.

An advantage of the mode of administration of the LAP formulations comprising the first and second compound and (I) is that high $C_{min}$ levels can be achieved without a commensurate high $C_{max}$, which could mitigate potential side effects associated with $C_{max}$.

The effective amount of the first and second compounds and optional third compound to be administered may be selected such that the blood plasma concentrations in a subject are kept during a prolonged period of time at a level between a maximum plasma level (or $C_{max}$) and the minimum blood plasma level (or $C_{min}$).

In some embodiments the blood plasma level of the compounds in a subject may be kept between the minimum blood plasma level (or $C_{min}$ as specified above) and the lower maximum plasma level of compound (I) (or $C_{max}$) which is defined as the level that corresponds to the lowest blood plasma level where the compounds act therapeutically. The lowest level where the compounds act therapeutically is the lowest blood plasma level that is effective in inhibiting replication of HIV in individuals infected by HIV so that the viral load of HIV is relatively low, for example where the viral load (represented as the number of copies of viral RNA in a specified volume of serum) is below about 200 copies/ml, in particular below about 100 copies/ml, more particularly below 50 copies/ml, specifically below the detection limit of the assay for HIV.

As mentioned above, the blood plasma levels of the compounds depend on the amount of active ingredient in each parenteral dosage administered. However, it also depends on the frequency of the administrations (i.e. the time interval between each administration). Both parameters can be used to direct the blood plasma levels to the desired values. The dose may be higher where administrations are less frequent.

Although the plasma levels of the compounds should remain below a maximum or above a minimum value, they may surpass the maximal value or drop below the minimal value during relatively short periods of time, which may be as short as possible. The maximum and minimum plasma levels therefore can be expressed as mean plasma levels during a certain period of time.

In some instances there may be a small initial plasma concentration peak shortly after administration, after which the plasma levels achieve a steady-state.

The compositions of the present invention conveniently allow administration of the first and second compound and optional third compound in unit dosage form containing, for example, from about 1 mg to about 1000 mg, from about 20 mg to about 100 mg, from about 20 mg to about 300 mg, from about 25 mg to about 800 mg, from about 25 mg to about 100 mg, from about 100 mg to about 200 mg, from about 200 mg to about 400 mg, from about 100 mg to about 800 mg, from about 100 mg to about 600 mg, from about 100 mg to about 400 mg per unit dosage form, or from about 400 mg to about 800 mg. In one embodiment, the unit dose is from about 100 mg to about 200 mg, which is administered to the subject once every month. In some embodiments, there could be an initially loading dose that is substantially higher than the later maintenance dose. Therefore, in one embodiment, the first compound is administered initially to the subject as a loading dose in amount that ranges from 400 mg to 800 mg and then is administered as a maintenance dose thereafter in an amount that ranges from about 20 mg to about 300 mg. In another embodiment, the subject could be dosed initially with 800 mg, then dosed at 100 mg thereafter.

The unit dose concentration of the first and second compound and optional third compound in the formulation may be selected from any of the following ranges: 0.05-0.5 µM, 0.5 to 1 µM, 1-5 µM, 5-25 µM, 25-50 µM, or 50-150 µM.

The dose to be administered may be calculated on a basis of about 1 mg/day to about 50 mg/day, preferably 3 mg/day to about 30 mg/day. This corresponds to a weekly dose of about 7 mg to about 350 mg, preferably about 20 mg to about 200 mg, or to a monthly dose of about 30 mg to about 1500 mg, preferably about 90 mg to about 900 mg. Doses for other dosing regimens can readily be calculated by multiplying the daily dose with the number of days between each administration.

The dose to be administered may be calculated on a basis of about 0.001 mg/kg//day to about 1 mg/kg/day, preferably 0.05 mg/kg/day to about 0.5 mg/kg/day. This corresponds to a weekly dose of about 0.5 mg to about 500 mg, preferably about 20 mg to about 200 mg, or to a monthly dose of about 30 mg to about 1500 mg, preferably about 90 mg to about 900 mg. Doses for other dosing regimens can readily be calculated by multiplying the daily dose with the number of days between each administration.

Once administered, the blood plasma levels of the first and second compounds and optional third compound in a subject may be more or less stable. After initial rise of the blood plasma levels, a steady state mode may be achieved during a prolonged period of time. By "steady state" is meant the condition in which the amount of drug present in the blood plasma of a subject stays at more or less the same level over a prolonged period of time. The plasma levels of the first and second compounds and optional third compound may then gradually decrease over time, and when the minimum plasma level is reached, then the next dose of first and second compounds and optional third compound may be administered. The term "stays at more or less the same level" does not exclude that there can be small fluctuations of the plasma concentrations within an acceptable range, for example, within about 30%, about 20%, or about 10%.

The parenteral compositions of the first and second compounds and optional third compound may be administered by intravenous injection or, preferably by subcutaneous or intramuscular administration.

The present invention is based on the use of parenteral compositions of the active ingredients comprising the first and second compounds and optional third compound and therefore the nature of the carrier is selected for suitability for parenteral administration. The carrier in most cases will comprise sterile water, in although other ingredients, for example, to aid solubility, may be included. Injectable solutions or suspensions, for example, may be prepared in which the carrier comprises saline solution, glucose solution or a mixture of saline and glucose solution. Further, the carrier may contain the surfactant system mentioned above such as polysorbate and polyethyleneglycol.

The parenteral pharmaceutical composition comprising the first and second compounds and optional third compound of the present invention is long-acting. Accordingly, the composition is useful for the treatment or prevention of HIV infection with administration at long time intervals, compared with conventional compositions or with other compounds similar to the first and second compounds and optional third compound in chemical structure. The compositions of the present invention can be intermittently administered to a patient, e.g., once per week, once per month, once per every 2 months, or one per every 3 months. In one embodiment, the compositions of the present invention could be administered at higher dosages (e.g., 800 mg) as a "loading dose" for the first one to three months, while after the first one to months the dosage could be lowered.

Therefore, the compositions of the present invention and an administration by subcutaneous (SC) or intramuscular (IM) injection using the same can lead to a remarkable reduction in medication (pill) burden or difficulty in patient compliance. Further, such intermittent administration of a composition of the present invention can contribute to maintaining therapy at appropriate compliance which leads to prevention of emergence of drug resistant HIV and maintaining the efficacy of therapy for an extended period of time.

In embodiment, the first compound formulation is a liquid suspension form for a bolus intramuscular or subcutaneous administration at a concentration ranges from 10 mg/ml to 250 mg/ml and having an injection volume of up to 4 ml (e.g., 2 injections, each 2 ml).

EXAMPLES

The following examples further describe and exemplify particular embodiments within the scope of the present Invention. The examples are given solely for illustration and are not to be construed as limitations as many variations are possible without departing from spirit and scope of the Invention.

The first compound may be synthesized by one of skill in the art by following the teachings of PCT Published Application No. WO2013090664 deriving from U.S. Provisional Application 61/57,6448, filed Dec. 16, 2011 which disclose a class of compounds useful in the treatment of HIV infection and AIDS.

A Thermo Orion 9110DJWP microelectrode and a Metrohmn 827 pH Meter were used for pH measurements. An Advanced Micro-Osmometer 3320 was used for osmolarity measurements. A Retsch PM400 planetary mill was used for wet bead milling.

Example 1

Preparation of LAP Vehicle 1.0 g of Polysorbate 80 was added to a 0.5 L volumetric flask. About 100 mL of Water for Injection (WFI) was added to the flask to dissolve. 8.5 g of Plasdone K29/32 was added to the flask with an additional 300 mL of WFI. The contents were stirred with a stir bar to dissolve. Phosphate buffer: 0.11039 g $NaH_2PO_4$; 0.27598 g $NaH_2PO_4:H_2O$; and 0.22572 g $Na_2HPO_4$ along with 4.16389 g NaCl as isotonicity agent was added. The mixture was again stirred to dissolve and then was q.s. to 500 mL. The solution was filtered through a 0.22 micrometer Corning filter. The resultant LAP vehicle was 1.7% w/v Plasdone K29/32 and 0.2% w/v Polysorbate 80 in phosphate buffer: 0.004M $NaH_2Po_4$ and 0.006M $Na_2HPO_4$.

Example 2

Homogenized Suspension Compositions (a) 2.5 mg/ml Homogenized Solution of the First Compound in LAP Vehicle for Subcutaneous Injection(SQ).

17.5 mg of the first compound was added to a clear 10 ml sterile vial with a crimp cap. The LAP Vehicle (as prepared in Example 1) was added to a weight of 7 grams. The solution was homogenized using a handheld Polytron PT1200F homogenizer for 1-2 minutes with a speed increasing from low to near max. The solution was then stirred at ambient room temperature. The resulting title solution had an osmolarity of 299 mOsm/kg and pH of 6.92. The solution was utilized for 5 mg/kg SQ injections.

(b) 10.0 mg/ml Homogenized Solution of the First Compound in LAP Vehicle for SC and IM (Intra-Muscular) Injection 80 mg of the first compound was added to a clear 10 ml sterile vial with a crimp cap. The LAP Vehicle (as prepared in Example 1) was added to a weight of 8 grams. The solution was homogenized using a handheld Polytron PT1200F homogenizer for 1-2 minutes with a speed increasing from low to near max. The solution was then stirred at ambient room temperature. The resulting title solution had an osmolarity of 300 mOsm/kg and pH of 7.25. The solution was utilized for 5 mg/kg IM injections and 20 mg/kg SQ injections.

(c) 25.0 mg/ml Homogenized Solution of the First Compound in LAP Vehicle for SC and IM (Intra-Muscular) Injection 250 mg of the first compound was added to a clear 20 ml sterile vial with a crimp cap. The LAP Vehicle (as prepared in Example 1) was added to a weight of 10 grams. The solution was homogenized using a handheld Polytron PT1200F homogenizer for 1-2 minutes with a speed increasing from low to near max. The solution was then stirred at ambient room temperature. The resulting title solution had an osmolarity of 323 mOsm/kg and pH of 7.68. The solution was utilized for 2.5 mg/kg IM injections and 2.5 mg/kg SQ injections.

(d) 40.0 mg/ml Homogenized Solution of the First Compound in LAP Vehicle for IM Injection 160 mg of the first compound was added to a clear 5 ml sterile vial with a crimp cap. The LAP Vehicle (as prepared in Example 1) was added to a weight of 4 grams. The solution was homogenized using a handheld Polytron PT1200F homogenizer for 1-2 minutes with a speed increasing from low to near max. The solution was then stirred at ambient room temperature. The resulting title solution had an osmolarity of 329 mOsm/kg and pH of 7.87. The solution was used for 20 mg/kg IM injections.

Example 3

Wet Bead Milling Formulations (a) Preparation of Wet Bead Milled Stock Suspension of the First Compound in LAP Vehicle 500 mg of the first compound is weighed into a 50 mL milling vessel. compound of Formula I was added to a clear 10 ml sterile vial with a crimp cap. The LAP Vehicle (as prepared in Example 1) was added to a weight of 10 grams thereby yielding a 100 mg/ml suspension. Beads were added at 4× suspension volume and the milling vessel was sealed with security tape. Milling was started at 250 rpm for 3 hours using a planetary mill PM400 with a 15 minute interval. After 3 hours the milling vessel was left in the planetary mill overnight at ambient room temperature. The beads were filtered using a 25 mm Easy pressure Syringe Filter Holder (screen size: 149 micrometers). A milky suspension was collected and stirred with a stir bar to defoam. The resulting wet bead milled (WBM) suspension had an osmolarity of 303 mOsm/kg and pH of 7.2. The solution was utilized for preparing the WBM suspensions following.

(b) 10.0 mg/ml WBM Suspension of the First Compound in LAP Vehicle for IM Injection 0.426 g of WBM suspension of Example 3(a) was added to a clear 5 ml sterile vial with a crimp cap. The LAP Vehicle (as prepared in Example 1) was added to a weight of 2 grams. The contents were swirled to mix. The resulting title solution had a pH of 6.87. The solution was utilized for 5 mg/kg IM injections.

(c) 2.5 mg/ml WBM Suspension of the First Compound in LAP Vehicle for SQ Injection 0.266 g of WBM suspension of Example 3(a) was added to a clear 10 ml sterile vial with a crimp cap. The LAP Vehicle (as prepared in Example 1) was added to a weight of 5 grams. The contents were swirled to mix. The resulting title solution had a pH of 6.78. The solution was utilized for 5 mg/kg SQ injections.

Injections were made in Sprague-Dawley rats SQ and IM at 5 and 20 mg/kg doses with $T_{1/2}$, $C_{max}$, $T_{max}$, and AUC being measured. Results are shown in Table 1 and FIG. 1. In FIG. 1 the human protein adjusted $IC_{90}$=4.31 ng/mL; the y-axis was a LAP concentration mean (n=3 per IM/SQ route); $T_{1/2}$ IV=3.4 hours; and $AUC_{0-24}$ IV=2.96 hr*microgram/mL.

TABLE 1

| Route of Administration | Dose | $T_{1/2}$ (days) | $C_{max}$ (ng/ml) | $T_{max}$ (h) | $AUC_{0-t}$ (h * μg/ml) |
|---|---|---|---|---|---|
| SQ | 5 | 5.0 ± 2.2 | 170.3 ± 9.2 | 6.7 ± 2.3 | [a]8.0 ± 0.5 |
|  | 20 | 19.3 ± 9.5 | 284.7 ± 48.4 | 6.7 ± 2.3 | [b]23.9 ± 7.2 |
| IM | 5 | 6.2 ± 2.5 | 100.3 ± 7.8 | 5.3 ± 2.3 | [c]7.7 ± 1.0 |
|  | 20 | 12.4 ± 5.1 | 177.7 ± 56.9 | 8.0 ± 4.0 | [d]24.9 ± 9.5 |

[a]= 24 days;
[b]= 57 days;
[c]= 17 days; and
[d]= 42 days

Figure 2:
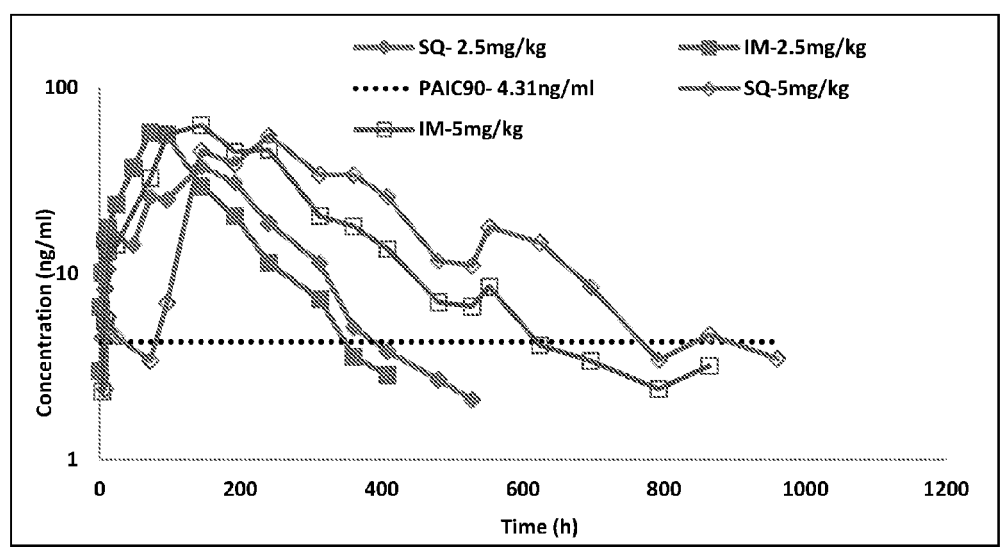
FIG. 2 depicts a plot of LAP Mean Concentration of the first compound versus time in hours of a LAP Dog PK study at 2.5 mg/kg and 5 mg/kg doses.

Injections were also made in Beagle dogs SQ and IM at 5 and 20 mg/kg doses with $T_{1/2}$, $C_{max}$, $T_{max}$, and AUC measured. Results are shown in Table 2 and FIG. 2. In FIG. 2 the human protein adjusted $IC_{90}$=4.31 ng/mL; the y-axis was a LAP concentration mean (n=3 per IM/SQ route); $T_{1/2}$ IV=6.9 hours; and $AUC_{0-24}$ IV=4.15 hr*microgram/mL.

TABLE 2

| Route of administration | Dose mg/kg | $T_{1/2}$ (days) | $C_{max}$ (ng/ml) | $T_{max}$ (h) | $AUC_{0-t}$ (h * μg/ml) |
|---|---|---|---|---|---|
| SQ | 2.5 | 4 ± 3 | 38.0 ± 11.0 | 144 ± 0 | [a]7.9 ± 1.9 |
|  | 5 | 5.3 ± 2.3 | 59.0 ± 14.5 | 208 ± 55.4 | [b]17.4 ± 1.4 |
| IM | 2.5 | 3 ± 3 | 59.3 ± 23.2 | 80.0 ± 13.9 | [c]8.6 ± 2.0 |
|  | 5 | 4.9 ± 1.1 | 69.7 ± 7.2 | 128.0 ± 27.7 | [d]16.2 ± 1.9 |

[a]= 22 days;
[b]= 40 days;
[c]= 17 days; and
[d]= 36 days

Example 4

Experimental Procedure for Rat LAP Study

For one formulation, if a particle size ($D_{50}$) of >1 μm is desired, the drug (the first compound) is either directly suspended into the aqueous buffer solution, or firstly milled by air milling into a more desirable particle size then followed by the suspension. In such cases, the suspension was prepared by weighing the drug and the buffer solution components into a suitable container followed by adding water for injection. The mixture was then vortexed until a uniform suspension was formed without visible agglomerates. Additional water for injection was then added to the target volume. Alternatively, if a particle size ($D_{50}$) of <1 µm is desired, the drug is firstly suspended into the buffer solution as stated above, then subjected to bead milling or microfluidization process in order to reduce the particle size to the submicron range. The prepared suspension is then subjected to a terminal sterilization by γ-irradiation at a minimum dose of 25 kGy.

For a second formulation, the drug (the first compound) and selected encapsulating polymer were co-dissolved in a suitable organic solvent, wherein the organic solvent met the following criteria: a) had a good solubility for the first compound and the selected polymer, b) was not miscible with water; c) had a low boiling point, thus a good volatility. Suitable organic solvents are; for example, methylene chloride (used in this Example), chloroform, ethyl acetate, ethyl formate, etc. The solution was then mixed at a volume ratio 1:2 to 1:100 with water containing 0.1-10% (w/v) surfactant selected from polyvinyl alcohol (PVA-1% PVA used in this Example), polyvinyl pyrrolidone (PVP), poloxamers, polysorbates, polyethoxylated castor oil, tocopheryl polyethylene glycol succinate, etc, to form a uniform emulsion. The emulsion was then subjected to vacuum evaporation to completely remove the volatile organic solvent, for example, in a rotorvap. The uniform suspension was then centrifuged and the resulting pellet was washed with water for injection 3 times to remove the surfactant. The washed pellet was then resuspended by water for injection in a suitable container followed by freeze drying into powdery microparticles encapsulating the first compound. The microparticles were then finally subjected to a terminal sterilization by γ-irradiation on dry ice at a minimum dose of 25 kGy.

Microparticle A: (Drug: RESOMER™ biodegradable polymer 752S 1:1)

Microparticle B: (Drug: RESOMER™ biodegradable polymer 752S 1:2)

Figure 3:
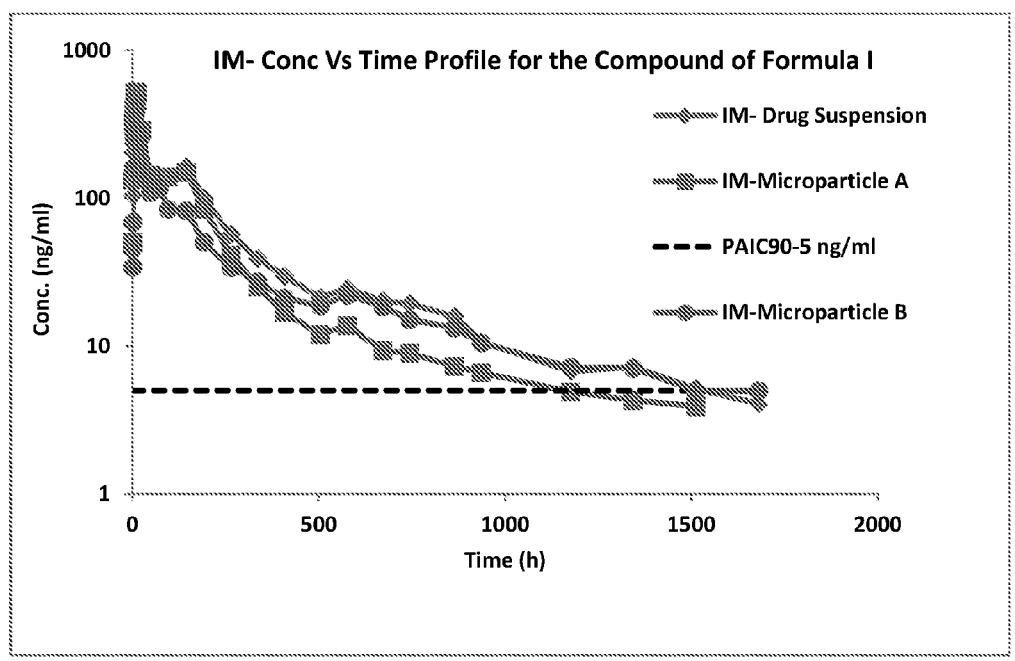
FIG. 3 depicts a plot of LAP Mean Concentration of the first compound versus time in hours of a LAP Rat (IM) PK study for different drug microparticle formulations

On the day of the study, the microparticle A (first compound: RESOMER™biodegradable polymer 752S 1:1) and B (first compound: RESOMER™ biodegradable polymer 752S 1:2) were mixed with 0.912 and 0.945 ml of vehicle, respectively, by vortexing until a visually uniform suspension was obtained with no large agglomerates. The drug suspension was already formulated as a uniform 1 ml suspension and was re-suspended by vortexing until a visually uniform suspension was obtained with no large agglomerates. Three male Crl:CD rats per formulation were dosed and sampled for the intramuscular route of administration of the first compound. The intramuscular dose of the first compound was administered as a single dose of 20 mg/kg and at a dose volume of 0.5 ml/kg. Blood samples were collected at 0.5, 1, 2, 4, 6, 8, 12, and 24 hours and up to 1680 hours post dose adminsitration. For each time point after dosing, approximately 0.1 ml blood samples were collected through tail-snip method, and immediately frozen and stored at −70 ° C. until analysis. Rat blood samples were then analyzed for the concentrations of the first compound using a method based on protein precipitation followed by LC-MS/MS analysis. The results of this Example are shown in Table 3 and graphed in FIG. 3.

TABLE 3

| Route (Dose) | Formulation | $T_{1/2}$ (days) | $C_{max}$ (ng/ml) | $T_{max}$ (hr) | $AUC_{0-1680\ h/70\ days}$ (h * mg/ml) |
|---|---|---|---|---|---|
| IM 5 mg/kg | Drug Suspension | 16 ± 0.6 | 284.0 ± 129.8 | 5.3 ± 2.3 | 56.5 ± 18.7 |
| IM 5 mg/kg | Microparticle A | 11 ± 5.7 | 612.7 ± 143.4 | 8.7 ± 3.1 | 49.5 ± 7.8 |
| IM 5 mg/ig | Microparticle B | 10.0 ± 3.5 | 424.7 ± 82.4 | 10.0 ± 3.5 | 46.2 ± 5.3 |

What is claimed:

1. A long acting parenteral (LAP) pharmaceutical composition comprising a pharmaceutically acceptable excipient and a first compound of the structure:

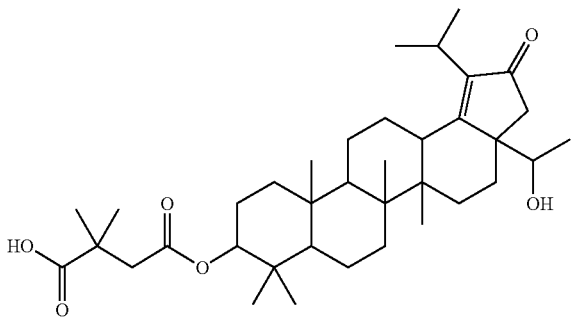

or a pharmaceutically acceptable salt thereof, in combination with a second compound of the structure:

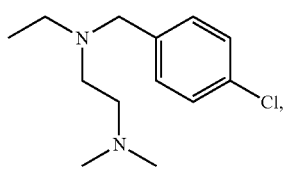

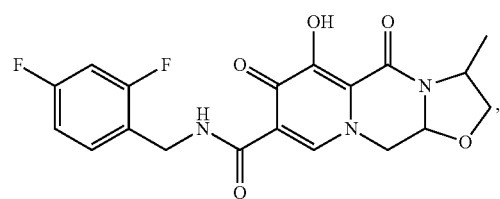 [SMILES: CC1COC2Cn3cc(C(=O)NCc4ccc(F)cc4F)c(=O)c(O)c3C(=O)N12]

or a pharmaceutically acceptable salt thereof.

2. A long acting parenteral (LAP) pharmaceutical composition comprising a pharmaceutically acceptable excipient and a first compound of the structure:

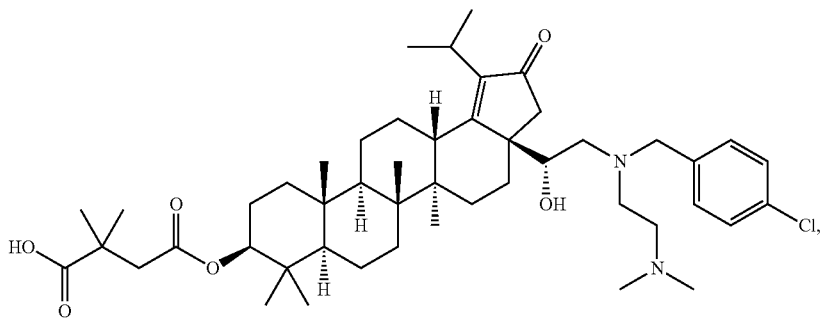

or a pharmaceutically acceptable salt thereof,
in combination with a second compound of the structure:

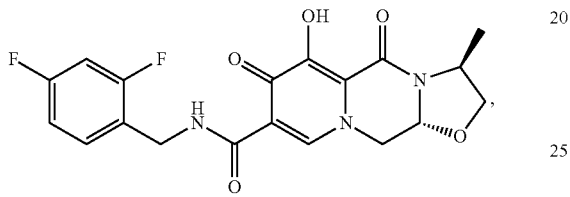

or a pharmaceutically acceptable salt thereof.

3. A long acting parenteral (LAP) pharmaceutical composition comprising a pharmaceutically acceptable excipient and a first compound of the structure:

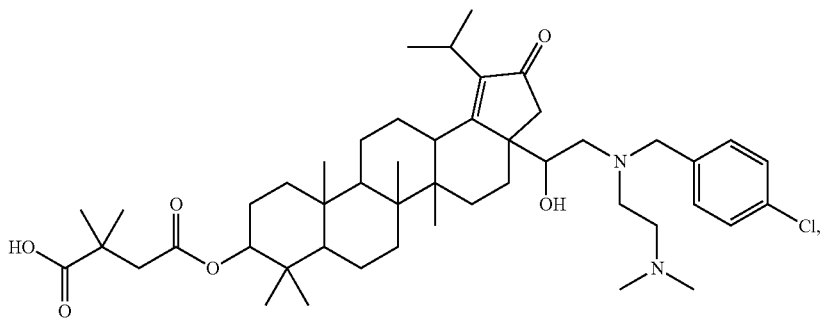

or a pharmaceutically acceptable salt thereof,
in combination with:
a) a second compound of the structure:

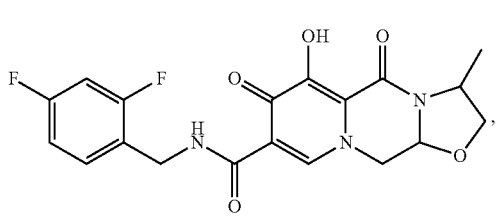 [SMILES: CC1COC2Cn3cc(C(=O)NCc4ccc(F)cc4F)c(=O)c(O)c3C(=O)N12]

or a pharmaceutically acceptable salt thereof, and b) a third compound, TMC-278 of the structure:

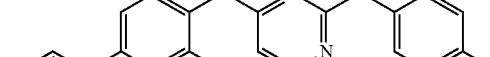

4. A long acting parenteral (LAP) pharmaceutical composition comprising a pharmaceutically acceptable excipient and a first compound of the structure:

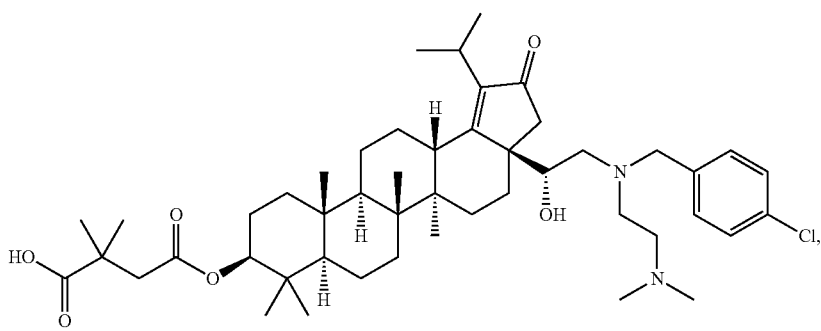

or a pharmaceutically acceptable salt thereof,
in combination with:
a) a second compound of the structure:

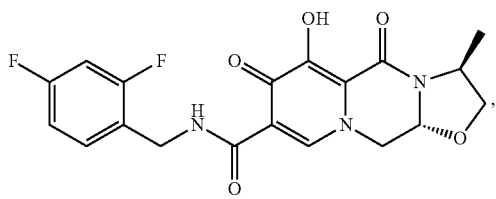 [SMILES: C[C@H]1CO[C@@H]2Cn3cc(C(=O)NCc4ccc(F)cc4F)c(=O)c(O)c3C(=O)N12]

or a pharmaceutically acceptable salt thereof, and
b) a third compound of the structure:

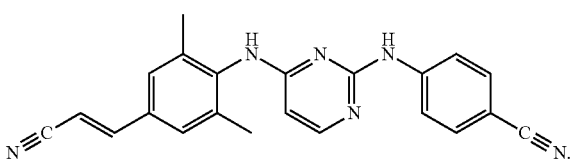 [SMILES: Cc1cc(/C=C/C#N)cc(C)c1Nc1ccnc(Nc2ccc(C#N)cc2)n1]

5. The pharmaceutical composition according to claim 1, further comprising a surfactant system.

6. The pharmaceutical composition according to claim 5, wherein the surfactant system comprises a surfactant in an amount ranging from 0.1% (w/v) to 3% (w/v) surfactant.

7. The pharmaceutical composition according to claim 5, wherein the surfactant system comprises a surfactant in an amount ranging from 0.2% (w/v) to 0.4% (w/v) surfactant.

8. The pharmaceutical composition according to claim 5, wherein the surfactant system comprises about 0.4% (w/v) surfactant.

9. The pharmaceutical composition according to claim 5, wherein the surfactant system comprises a surfactant selected from the group consisting of polyoxyethylene sorbitan fatty acid esters, poloxamers, sorbitan esters of fatty acids (SPAN), polyethoxylated castor oil and its derivatives, tocopheryl polyethylene glycol succinate, and polyvinyl alcohols.

10. The pharmaceutical composition according to claim 9, wherein the surfactant system comprises a surfactant that is a polysorbate.

11. The pharmaceutical composition according to claim 9, wherein the surfactant system comprises a surfactant that is polysorbate 80.

12. The pharmaceutical composition according to claim 9, wherein the surfactant system comprises a poloxamer.

13. The pharmaceutical composition according to claim 9, wherein the surfactant system comprises poloxamer 338.

14. The pharmaceutical composition according to claim 9, wherein the surfactant system comprises tocopheryl polyethylene glycol succinate.

15. The pharmaceutical composition according to claim 9, wherein the surfactant system comprises poloxamer 338 and tocopheryl polyethylene glycol succinate.

16. The pharmaceutical composition according to claim 5, wherein the surfactant system comprises a stabilizer that is selected from the group consisting of polyethylene glycols, carboxymethylcellulose calcium, carboxymethylcellulose sodium, methylcellulose, hydroxyethylcellulose, hydroxypropylcellulose, hydroxymethylpropylcellulose, polysaccharides, hyaluronic acid, polyvinyl alcohol (PVA) and polyvinylpyrrolidone (PVP).

17. The pharmaceutical composition according to claim 16, wherein the surfactant system comprises a stabilizer that is polyethylene glycol.

18. The pharmaceutical composition according to claim 17, wherein the surfactant system comprises a stabilizer that is PEG-3350.

19. The pharmaceutical composition according to claim 16, wherein the surfactant system comprises a stabilizer in an amount that ranges from 1% (w/v) to 5% (w/v) stabilizer.

20. The pharmaceutical composition according to claim 19, wherein the surfactant system comprises about 2% (w/v) stabilizer.

21. The pharmaceutical composition according to claim 5, wherein the surfactant system comprises a buffer salt.

22. The pharmaceutical composition according to claim 21, wherein the surfactant system comprises a buffer salt that is phosphate buffered saline.

23. The pharmaceutical composition according to claim 21, wherein the surfactant system comprises a buffer salt at a concentration of about 10 mM.

24. The pharmaceutical composition according to claim 1, wherein the first compound, second compound, or third compound is in a crystalline form prior to encapsulating into a microparticle and combining with a surfactant system.

25. The pharmaceutical composition according to claim 1, wherein the first compound, second compound, or third compound is in an amorphous microparticle form.

26. The pharmaceutical composition according to claim 1, wherein the first compound, second compound, or third compound is in a microparticle form, wherein the microparticles of the first compound, second compound, or third compound range in size from 0.05 μm to 100 μm.

27. The pharmaceutical composition according to claim 1, wherein the first compound, second compound, or third compound is in a microparticle form, wherein the microparticles of the first compound, second compound, or third compound range in size from 0.1 µm to 5 µm.

28. The pharmaceutical composition according to claim 1, wherein the first compound, second compound, or third compound is encapsulated in a polymer.

29. The pharmaceutical composition according to claim 28, wherein the first compound, second compound, or third compound is encapsulated in a polymer that comprises poly (lactic-co-glycolic) acid.

30. A method of treating an HIV infection in a subject in need thereof comprising administering to the subject of a long acting parenteral (LAP) pharmaceutical composition comprising a pharmaceutically acceptable excipient and a first compound of the structure:

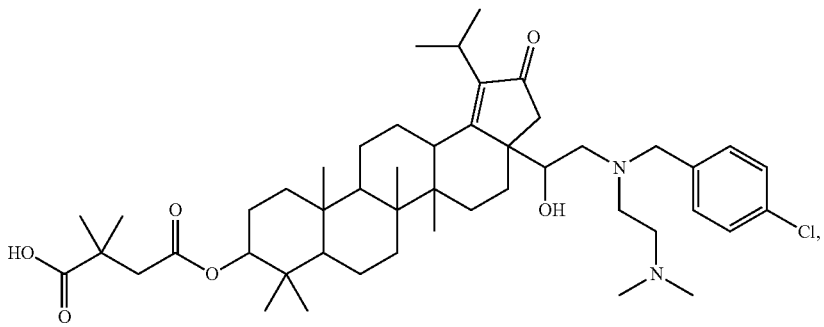

or a pharmaceutically acceptable salt thereof,
in combination with a second compound of the structure:

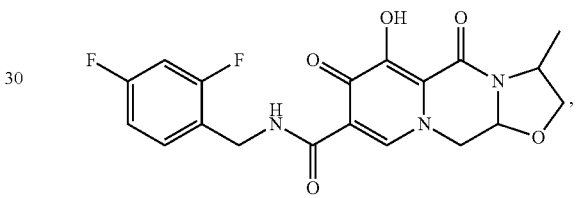

or a pharmaceutically acceptable salt thereof.

31. The method according to claim 30, wherein the administering is performed separately and each compound is administered in a long acting parenteral (LAP) pharmaceutical composition.

32. The method according to claim 30, wherein the administering is performed simultaneously in one long acting parenteral (LAP) pharmaceutical composition.

33. A method of treating an HIV infection in a subject in need thereof comprising administering to the subject a long acting parenteral (LAP) pharmaceutical composition comprising a pharmaceutically acceptable excipient and a first compound of the structure:

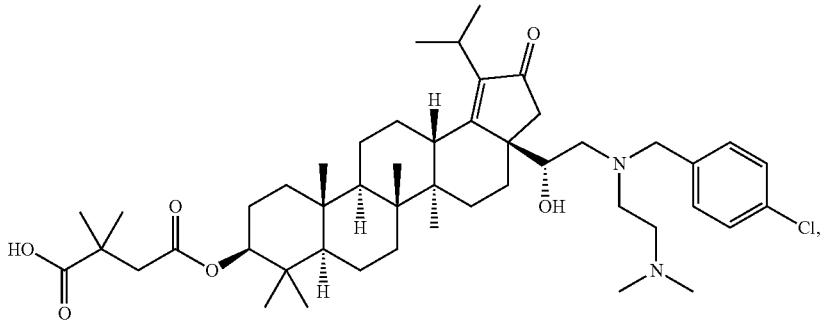

or a pharmaceutically acceptable salt thereof, in combination with a second compound of the structure:

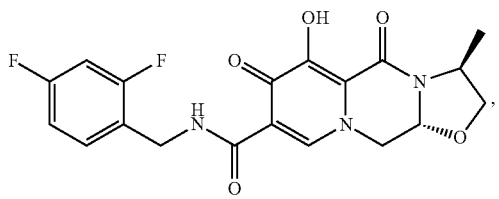 [SMILES: C[C@H]1CO[C@@H]2Cn3cc(C(=O)NCc4ccc(F)cc4F)c(=O)c(O)c3C(=O)N12]

or a pharmaceutically acceptable salt thereof.

34. The method according to claim 33, wherein the administering is performed separately and each compound is administered in a long acting parenteral (LAP) pharmaceutical composition.

35. The method according to claim 33, wherein the administering is performed simultaneously in one long acting parenteral (LAP) pharmaceutical composition.

36. A method of treating an HIV infection in a subject in need thereof comprising administering to the subject a long acting parenteral (LAP) pharmaceutical composition comprising a pharmaceutically acceptable excipient and a first compound of the structure:

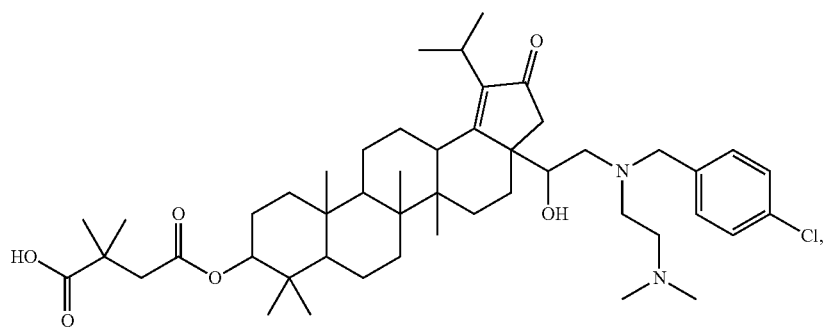

or a pharmaceutically acceptable salt thereof,
in combination with:
a) a second compound of the structure:

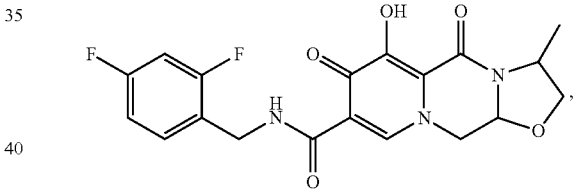

or a pharmaceutically acceptable salt thereof, and
b) a third compound of the structure:

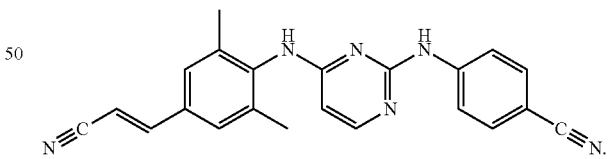

37. The method according to claim 36, wherein the administering is performed separately and each compound is administered in a long acting parenteral (LAP) pharmaceutical composition.

38. The method according to claim 36, wherein the administering is performed simultaneously in one long acting parenteral (LAP) pharmaceutical composition.

39. A method of treating an HIV infection in a subject in need thereof comprising administering to the subject a long acting parenteral (LAP) pharmaceutical composition comprising a pharmaceutically acceptable excipient and a compound of the structure:

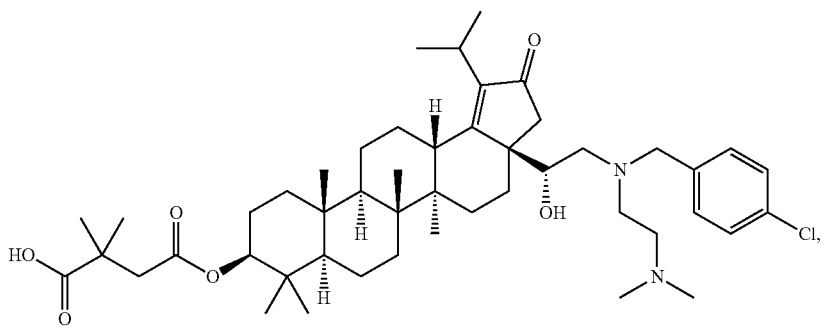

or a pharmaceutically acceptable salt thereof,
in combination with:
a) a second compound of the structure:

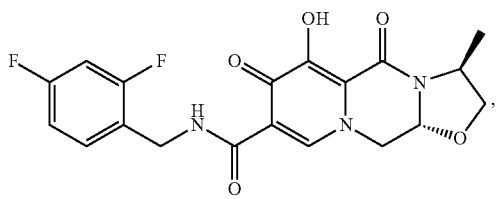 [SMILES: C[C@H]1CO[C@@H]2Cn3cc(C(=O)NCc4ccc(F)cc4F)c(=O)c(O)c3C(=O)N12]

or a pharmaceutically acceptable salt thereof, and
b) a third compound of the structure:

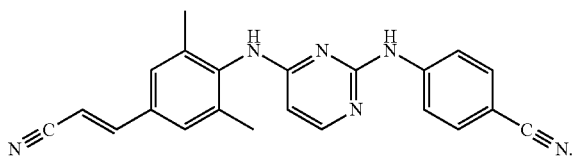 [SMILES: Cc1cc(/C=C/C#N)cc(C)c1Nc1ccnc(Nc2ccc(C#N)cc2)n1]

40. The method according to claim 39, wherein the administering is performed separately and each compound is administered in a long acting parenteral (LAP) pharmaceutical composition.

41. The method according to claim 39, wherein the administering is performed simultaneously in one long acting parenteral (LAP) pharmaceutical composition.

42. The method according to claim 30, wherein the subject is administered the LAP pharmaceutical composition including the first compound, second compound, or third compound, on a dosing regimen ranging from every week to every 6 months.

43. The method according to claim 42, wherein the subject is administered the LAP pharmaceutical composition on a dosing regimen ranging from every week to every three months.

44. The method according to claim 42, wherein the subject is administered the LAP pharmaceutical composition on a dosing regimen ranging from every week to every two months.

45. The method according to claim 42, wherein the subject is administered the LAP pharmaceutical composition on a dosing regimen that is monthly.

46. The pharmaceutical composition according to claim 1, wherein the first compound, second compound, or third compound is in a microparticle form, wherein the microparticles of the first compound, second compound, or third compound range in size from 0.05 µm to 100 µm, wherein said microparticles comprise substantially the same size.

47. The pharmaceutical composition according to claim 1, wherein the first compound, second compound, or third compound is in a microparticle form, wherein the microparticles of the first compound, second compound, or third compound range in size from 0.05 µm to 100 µm, wherein said microparticles comprise two or more substantially different particle sizes that provide for earlier and later release after administration to a subject and result in varying absorption kinetics therein.

48. The pharmaceutical composition according to claim 1, wherein the first compound, second compound, or third compound is in a microparticle form, wherein the microparticles of the first compound, second compound, or third compound range in size from 0.05 µm to 0.5 µm.

49. The pharmaceutical composition according to claim 1, wherein the first compound, second compound, or third compound is in a microparticle form, wherein the microparticles of the first compound range in size from 0.5 µm to 5 µm.

50. The pharmaceutical composition according to claim 1, wherein the first compound, second compound, or third compound is in a microparticle form, wherein the microparticles of the first compound, second compound, or third compound range in size from 5 µm to 25 µm.

51. The pharmaceutical composition according to claim 1, wherein first compound, second compound, or third compound is in a microparticle form, wherein the microparticles of the first compound, second compound, or third compound range in size from 25 µm to 100 µm.

52. The pharmaceutical composition according to claim 1, wherein the first compound, second compound, or third compound is present in an amount ranging from 20 mg to 100 mg.

53. The pharmaceutical composition according to claim 1, wherein the first compound, second compound, or third compound is present in an amount ranging from 100 mg to 200 mg.

54. The pharmaceutical composition according to claim 1, wherein the first compound, second compound, or third compound is present in an amount ranging from 200 mg to 400 mg.

55. The pharmaceutical composition according to claim 1, wherein the first compound, second compound, or third compound is present in an amount ranging from 400 mg to 800 mg.

56. The method according to claim 30, wherein the first compound, second compound, or third compound is administered initially to the subject as a loading dose in amount that ranges from 400 mg to 800 mg and then is administered as a maintenance dose thereafter in an amount that ranges from about 20 mg to about 300 mg.

57. The method according to claim 30, wherein the LAP compositions comprising the first compound, second compound, or third compound is administered to the subject only after the subject has been administered treatment comprising a generally accepted anti-retroviral regimen.

* * * * *